US011083874B2

(12) United States Patent
Hakky et al.

(10) Patent No.: US 11,083,874 B2
(45) Date of Patent: Aug. 10, 2021

(54) URINARY CATHETER SYSTEM WITH IMPROVED RETAINING STRUCTURE AND ENHANCED URINARY DRAINAGE

(71) Applicants: Said Ismail Hakky, Doral, FL (US); Shereen Said Hakky, Doral, FL (US); Shelaan Said Ismail Hakky, Doral, FL (US); Sahar Mahdi Nasser, Doral, FL (US)

(72) Inventors: Said Ismail Hakky, Doral, FL (US); Shereen Said Hakky, Doral, FL (US); Shelaan Said Ismail Hakky, Doral, FL (US); Sahar Mahdi Nasser, Doral, FL (US)

(73) Assignee: Lotus Medical Technologies, Doral, FL (US)

( * ) Notice: Subject to any disclaimer, the term of this patent is extended or adjusted under 35 U.S.C. 154(b) by 459 days.

(21) Appl. No.: 15/878,996

(22) Filed: Jan. 24, 2018

(65) Prior Publication Data
US 2019/0224455 A1    Jul. 25, 2019

(51) Int. Cl.
*A61M 25/04* (2006.01)
*A61M 39/22* (2006.01)
(Continued)

(52) U.S. Cl.
CPC ........ *A61M 25/04* (2013.01); *A61M 25/0017* (2013.01); *A61M 25/0074* (2013.01);
(Continued)

(58) Field of Classification Search
CPC .. A61B 2017/3484; A61M 2025/0024; A61M 2025/0079; A61M 2025/024;
(Continued)

(56) References Cited

U.S. PATENT DOCUMENTS 3,397,699 A * 8/1968 Kohl ...................... A61M 25/04
604/105
3,915,171 A * 10/1975 Shermeta ............ A61J 15/0065
604/101.05
(Continued)

*Primary Examiner* — Adam Marcetich
(74) *Attorney, Agent, or Firm* — Rosenberg, Klein & Lee

(57) ABSTRACT

A catheter has a double-action retention mechanism with (a) one retention mechanism having a reinforced retention body transformable into a deployed flower-like configuration when the catheter is inserted in the bodily cavity, and (b) a stabilizer securing the catheter to a patient's body to maintain a stable position. The retention mechanism for securing the catheter in the bodily cavity is configured with a thickened or reinforced wall portions of the retention body. The inner channel of the catheter body is wider than conventional catheters, thus attaining better drainage and better fluid flow. Due to the reinforced flower configuration, an inadvertent removal of the catheter with the flower configuration fully deployed will afflict no significant damage. When the catheter is to be removed, the catheter's body is disengaged from the stabilizer and the flower configuration of the retention mechanism retention body controllably collapses, thus transforming the catheter to a configuration suitable for removal of the catheter from the bodily cavity. The improved Catheter is simple in operation, safe, prevents from CAUTI, and provides a non-residual urine drainage and high flow rate.

13 Claims, 12 Drawing Sheets

(51) Int. Cl.
*A61M 25/00* (2006.01)
*A61M 25/02* (2006.01)
(52) U.S. Cl.
CPC ..... *A61M 39/223* (2013.01); *A61M 2025/024* (2013.01); *A61M 2025/028* (2013.01); *A61M 2025/0266* (2013.01); *A61M 2205/3344* (2013.01); *A61M 2210/1085* (2013.01)
(58) Field of Classification Search
CPC .. A61M 2025/0246; A61M 2025/0266; A61M 2025/028; A61M 2205/3344; A61M 2210/1085; A61M 25/0017; A61M 25/0074; A61M 25/04; A61M 39/223
See application file for complete search history.

(56) References Cited

U.S. PATENT DOCUMENTS

| | | | | |
|---|---|---|---|---|
| 4,029,099 | A * | 6/1977 | Fifield | A61M 39/08 604/326 |
| 4,154,242 | A * | 5/1979 | Termanini | A61M 25/04 604/105 |
| 4,397,647 | A * | 8/1983 | Gordon | A61M 25/02 128/DIG. 26 |
| 4,813,935 | A | 3/1989 | Haber et al. | |
| 5,197,971 | A * | 3/1993 | Bonutti | A61B 17/0218 604/105 |
| 5,935,107 | A * | 8/1999 | Taylor | A61J 15/0015 604/164.04 |
| 5,935,165 | A * | 8/1999 | Schouwenburg | A61F 2/203 623/9 |
| 5,976,068 | A * | 11/1999 | Hakky | A61F 2/0009 600/29 |
| 8,177,741 | B2 | 5/2012 | Hammack et al. | |
| 2003/0181939 | A1* | 9/2003 | Bonutti | A61M 29/02 606/192 |
| 2004/0181235 | A1* | 9/2004 | Daignault | A61M 25/04 606/108 |
| 2005/0049577 | A1* | 3/2005 | Snell | A61M 25/0009 604/544 |
| 2005/0101941 | A1* | 5/2005 | Hakky | A61M 25/0017 604/544 |
| 2005/0240280 | A1* | 10/2005 | Aliski | A61M 27/008 623/23.68 |
| 2007/0250036 | A1* | 10/2007 | Volk | A61M 25/0158 604/510 |
| 2008/0058730 | A1* | 3/2008 | Melsheimer | A61M 25/04 604/177 |
| 2010/0331825 | A1* | 12/2010 | Hakky | A61M 25/0074 604/544 |
| 2012/0116357 | A1* | 5/2012 | Hakky | A61M 25/02 604/544 |
| 2012/0136314 | A1* | 5/2012 | Ciccone | A61M 25/0017 604/174 |
| 2012/0238959 | A1* | 9/2012 | Thorne | A61M 25/02 604/177 |
| 2014/0046320 | A1* | 2/2014 | Kappel | A61B 17/00234 606/40 |
| 2014/0107610 | A1* | 4/2014 | Witte | A61M 25/04 604/500 |
| 2014/0276628 | A1* | 9/2014 | Gandras | A61M 25/04 604/514 |
| 2016/0271377 | A1* | 9/2016 | Pendleton | A61M 25/04 |

\* cited by examiner

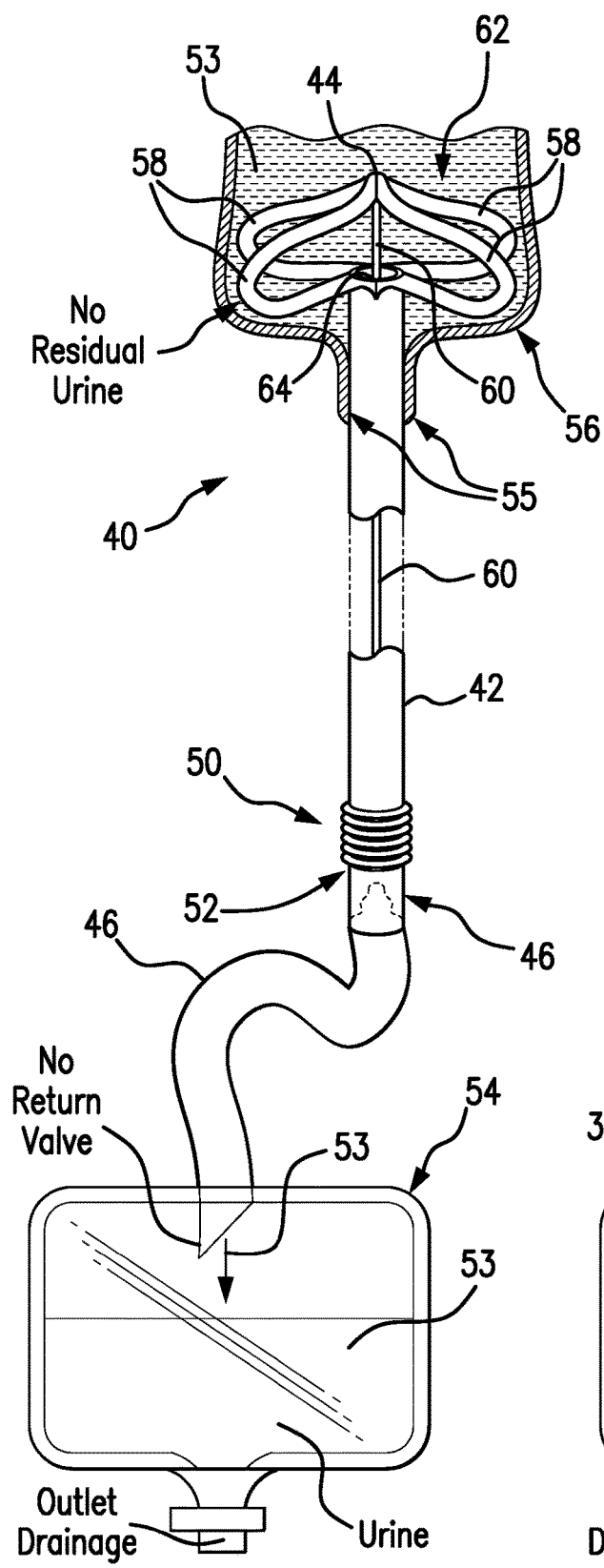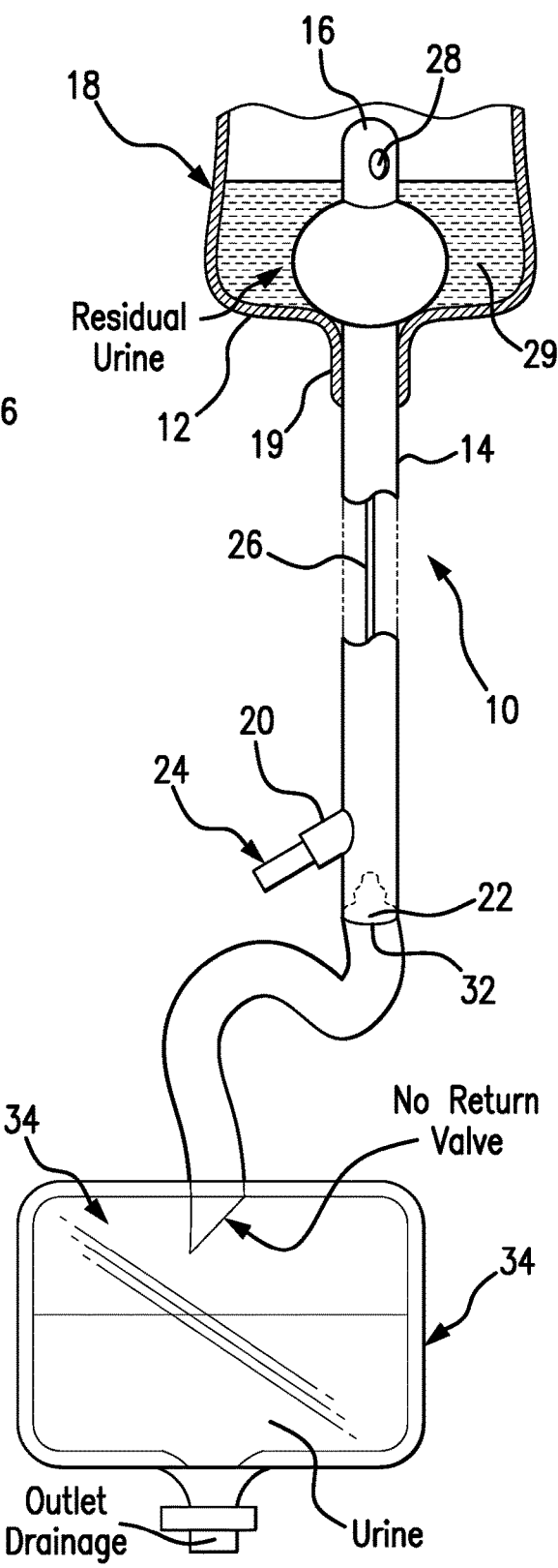
FIG. 2C PRIOR ART
FIG. 1C PRIOR ART

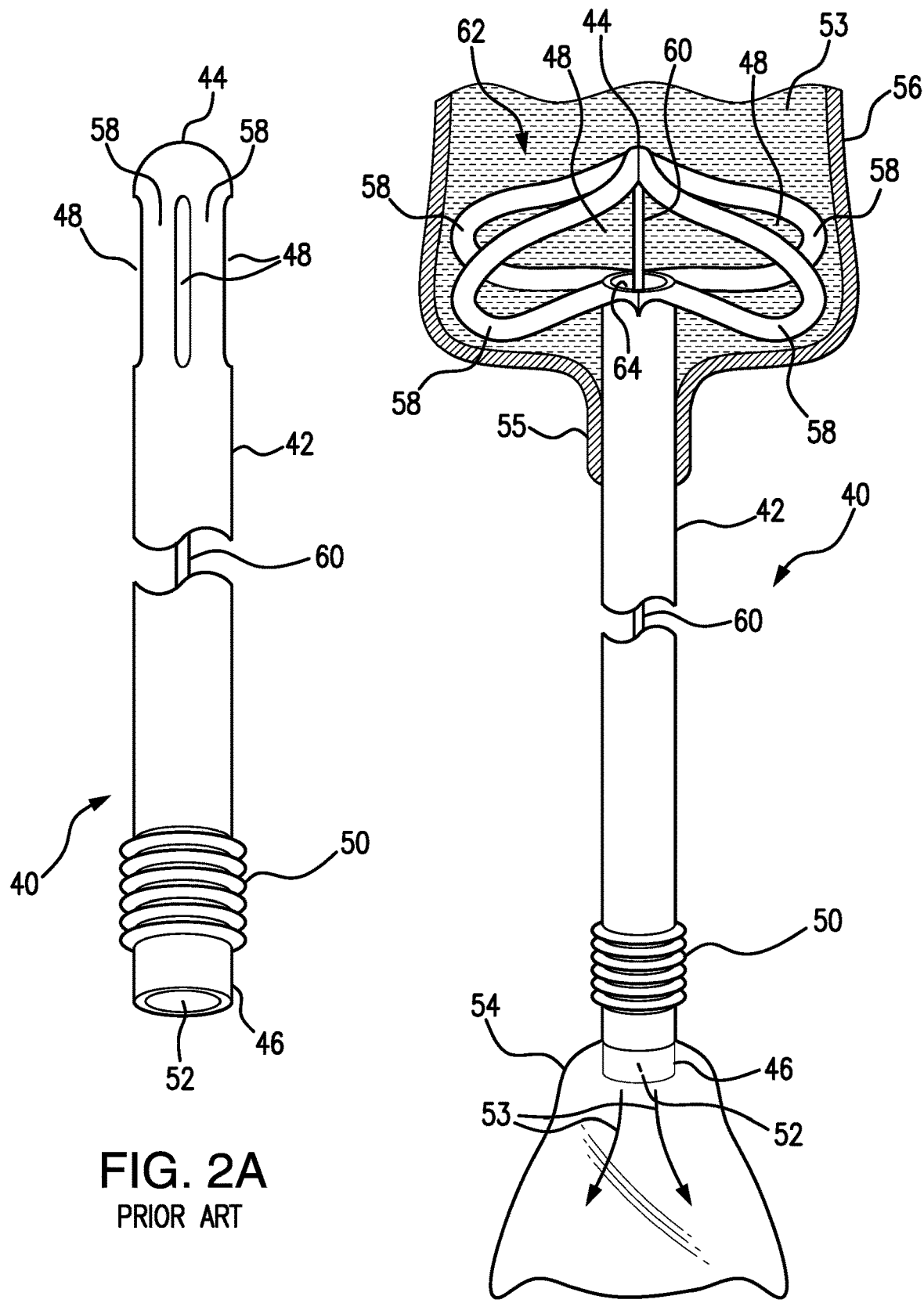

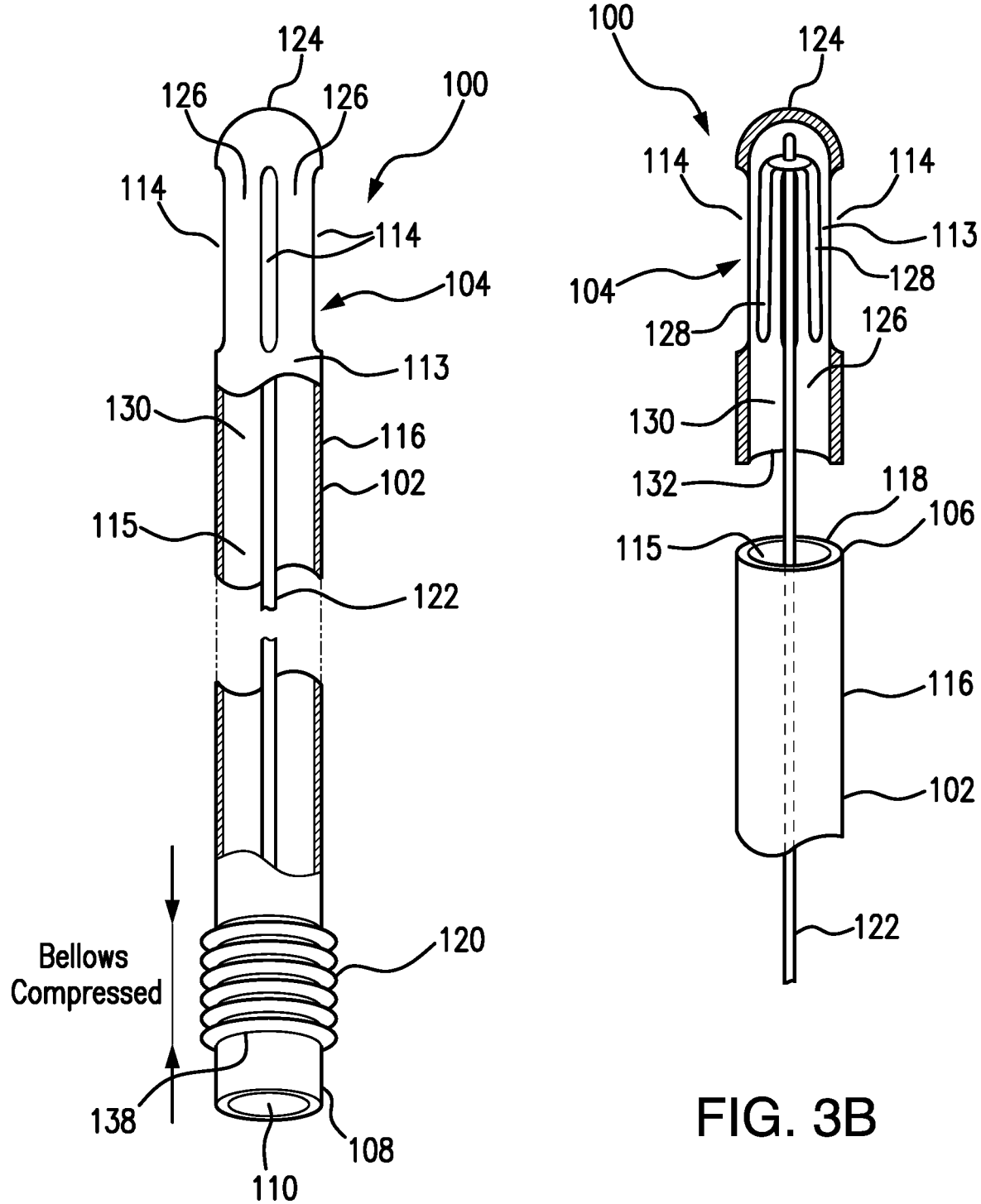

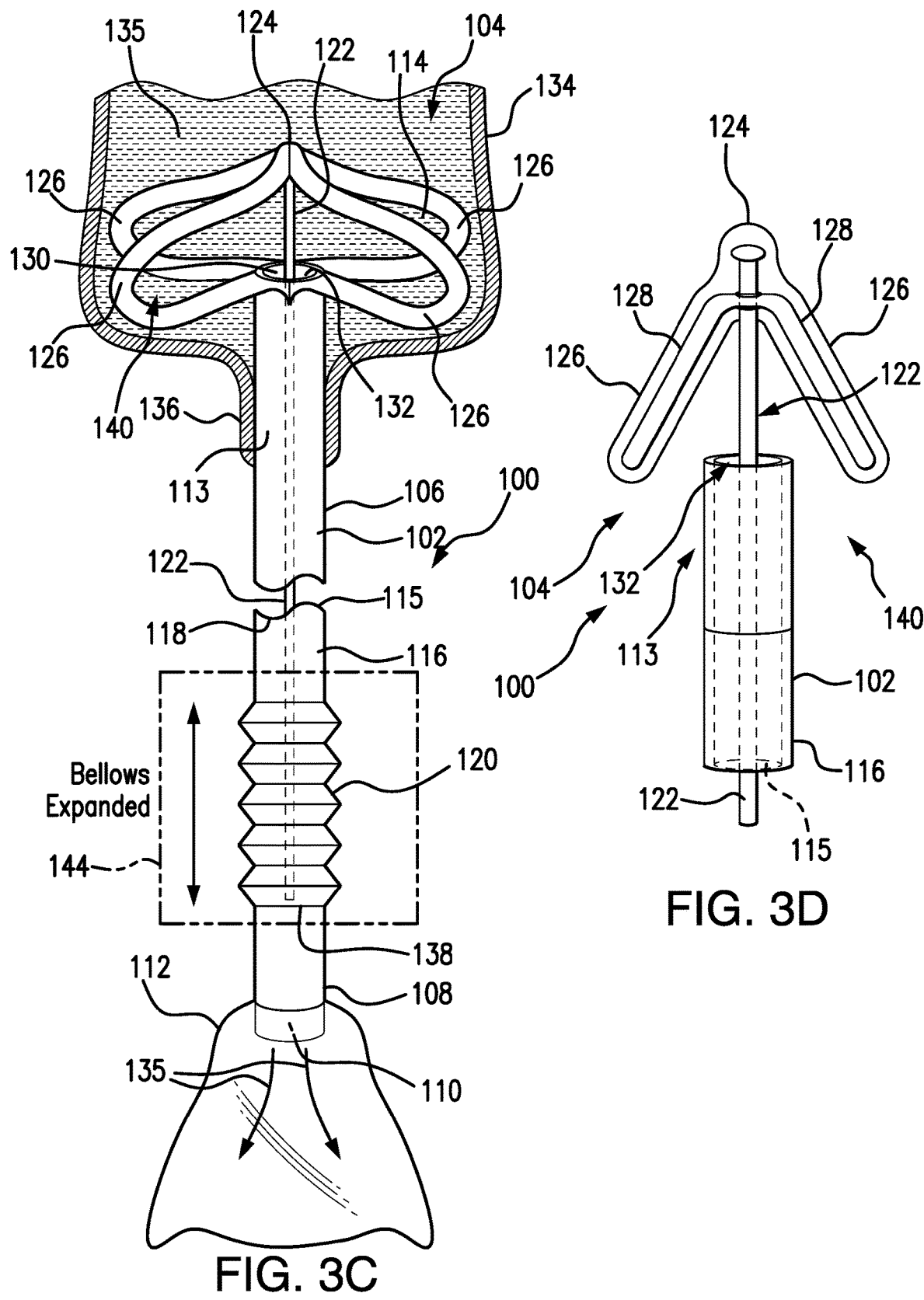

URINARY CATHETER SYSTEM WITH IMPROVED RETAINING STRUCTURE AND ENHANCED URINARY DRAINAGE

FIELD OF THE INVENTION

The present invention relates to surgical devices, and particularly, to catheters which are introduced into bodily cavities for drainage of bodily fluids therefrom, as well as for medication delivery to bodily cavities for irrigation and treatment.

More in particular, the present invention relates to a urinary catheter configured for improved safety to a patient through usage of a reliable retaining mechanism.

In addition, the present invention is directed to a urinary drainage device (urinary catheter) which provides an enhanced urinary flow and which leaves no residual urine in the bladder of a patient, thus decreasing occurrence of Catheter Associated Urinary Tract Infection (CAUTI).

BACKGROUND OF THE INVENTION

Indwelling urinary catheters are widely used in acute and chronic clinical cases. In acute clinical cases, a urinary catheter is usually inserted within the bladder of a patient through the urethra. Urine is drained from the bladder and collected in a urine bag for urine output measurements. This is a standard procedure used during major surgeries, or in intensive care unit settings.

The urine output measurement is indicative of the status of the kidney excretion. Thus, the measurement of urine output is important for correlation with continuous measurements of the vital signs of a patient, which include blood pressure, heart rate, temperature and pulse rate of a patient.

In acute settings, the urinary catheter may be left indwelled in the bladder for a period of time ranging from a few hours to a few days. In some cases, the indwelling of the urinary catheter may be for a longer extended time interval.

In the case of post-operative prostate or bladder surgeries, bleeding with or without clotting may occur. Clotting blocks the drainage port of a catheter. If the drainage of the bladder is blocked, the patient experiences severe pain that, if such persists, may lead to shock. Thus, clots must be flushed out, and blood must be diluted with fluids to prevent blood from further clotting.

In cases of continuous bleeding or gross hematuria setting, three way indwelling urinary catheters are conventionally used, which have three ports. One of the ports, i.e., the first port, is configured as a small first tube built within the walls of the catheter body. One end of the first tube is connected to an infusion bag, so that the fluids can be infused directly inside the bladder through another end of the first tube. Assisted by this mechanism, clots are flushed out, and blood is diluted in order to prevent further clotting of the blood.

A second port of the three-way catheter is configured as a small second tube which is also built within the walls of the catheter body. At one end, the second tube is connected to a balloon used as a retaining mechanism for securing the catheter within the bladder. Another end of the second tube is connected to a two-way valve operating to either inflate the balloon with a sterile fluid, or deflate the balloon by removing the sterile fluid therefrom to permit removal of the catheter from the bladder.

A third port of the three-way catheter is associated with an internal channel of the catheter body through which the urine is drained from the bladder to a urine collection bag.

At times, two-way or three-way catheters are used for administering medication into the bladder to treat certain pathologies of the bladder, such as, for example, superficial cancers of the bladder.

In chronic clinical settings, urinary catheters are used generally in a permanent manner for patients who are unable to urinate by themselves. The preferred approach for introduction of the urinary catheter into the bladder in such chronic cases is called supra-pubic catheterization where the catheter is inserted through the anterior abdominal wall of a patient. In accordance with this methodology, a urinary catheter is connected through the anterior abdominal wall into the bladder, and is left in place for extended periods of times ranging over months, years, or possibly for the life of the patient.

Several types of urinary catheters are currently used for urinary patients, such as: (a) straight catheter for intermittent catheterization, (b) Foley urinary balloon catheter, and (c) No-Balloon "Lotus" urinary catheter. The Foley and No-Balloon Catheters are the only two catheters which could be retained within the bladder (Indwelling). U.S. Pat. Nos. 4,813,935 and 8,177,741 detail the principles of the Foley urinary balloon and No-Balloon "Lotus" catheter, respectively.

As shown in FIGS. 1A, 1B, and 1C, the Foley urinary balloon catheter 10 is provided with a retaining mechanism operating with an inflatable/deflatable balloon 12 configured to retain the catheter in place when inserted into the bladder 18. The Foley urinary balloon catheter 10 is formed with an elastic tube 14 having a proximal tip 16 for insertion through the urethra 19 into the urinary bladder 18.

A two-way valve mechanism 20 is disposed at a distal end 22 of the catheter 10. The two-way valve 20 has a port 24 through which a sterile fluid 25 is injected into or withdrawn from the balloon 12.

As shown in FIG. 1A, depicting the catheter 10 in the passive configuration, the balloon 12 is deflated, and the catheter 10 is suitable for insertion to or removal from the bladder 18 through the urethra 19.

In addition, a urine bag 34 is attached to the distal end 22 of the tube 14 in operative coupling to the urine exhaust port 32 through which the urine from the bladder is removed from the catheter into the urine bag 34.

As shown in FIG. 1B, depicting the catheter the active state, for activation of the retaining mechanism of the Foley urinary balloon catheter 10, the sterile fluid 25 is injected through a syringe (not shown) into the port 24 of the two-way valve mechanism 20 which is fluidly connected to the balloon 12 through a channel 26 extending within the tube 14 of the catheter 10. The sterile fluid 25, which is injected into the port 24, flows through the channel 26 to the balloon forming membrane 27 and inflates the balloon 12. When the balloon 12 is inflated, it secures the catheter 10 in place within the bladder 18, so that the catheter 10 is fixed within the bladder 18 for the necessary time duration.

With the balloon 12 inflated by injecting the sterile fluid 25, the two-way valve 20 prevents the fluid 25 from escaping from the inflated balloon 12 while the catheter 10 remains indwelled inside the urinary bladder 18 of the patient.

The Foley Catheter 10 depends totally on the bladder neck for remaining in position inside the bladder 18. This makes the Foley Catheter extremely unsafe in the case of inadvertent removal due to containment of water (which is not compressible) in the balloon (having a volume of 20 c.c.-30 c.c.). Unfortunately, the inadvertent removal of the Foley Catheter with the balloon fully inflated is common in dementia patients, patients recovering from anesthesia, psychotic patients, or semi-comatose or confused patients. An inadvertent removal of the Foley Catheter from the bladder with the balloon 12 fully inflated causes an immediate pain and bleeding due to tear of the bladder neck and the urethra. Inadvertent removal of the Foley catheter with the balloon fully inflated needs a force ranging between 25 Pounds and up to or more than 50 Pounds Force. The removal of the catheter with the inflated balloon, when such a force is applied, is extremely dangerous and may cause further complications, mainly in a form of urinary incontinence or stricture for the rest of the patient's life.

When the Foley urinary catheter 10 is to be removed purposely, the previously injected sterile fluid 25 is withdrawn from the balloon 12 through the port 24 of the two-way valve 20 by a syringe (not shown in FIGS. 1A-1B). The withdrawal of the sterile fluid 25 results in balloon deflation, so that the catheter can be removed from the bladder 18.

The proximal tip 16 of the catheter 10 which is introduced through the urethra 19 into the bladder 18 is formed with the urine exit (drainage) port 28. Through the urine exit port 28, urine 29 is drained from the bladder 18 through an inner lumen 30 of the catheter tube 14 to the exhaust port 32 at the distal end 22 of the catheter tube 14 which terminates in the urine collection bag 34.

Although being widely used, the Foley Catheter depends on a fluid filled balloon sitting at the bladder neck/Trigone. This makes the Foley Catheter unsafe, as described in previous paragraphs.

The Foley urinary balloon catheter also has other shortcomings, one of which is a balloon's inherited problem of failure to deflate upon sterile fluid withdrawal. This situation may necessitate a surgical intervention with anesthesia to burst the balloon. Another problem is that the balloon in the Foley catheter may at times be inadvertently inflated inside the urethra causing bleeding and urethra tear and possible long-lasting stricture formation of the urethra.

Furthermore, when indwelled, the balloon 12 of the Foley balloon catheter 10 generally leaves large amounts of the residual urine in the bladder due to the fact that the drainage port 28 of the Foley balloon catheter is located a substantial distance above the bladder neck, as shown in FIG. 1B. This is dictated by the positioning of the drainage port 28 close to the tip 16 of the catheter 10 (as depicted in FIG. 1A) and above the balloon 12.

The residual urine, which is collected at the bottom of the bladder below the level of the drainage port 28, cannot be removed, and remains in the bladder. The amount of the residual urine in the bladder may range from 20 c.c. up to 50 c.c., or greater. The residual urine 29 may cause continuous irritation of the bladder and CAUTI (Catheter Associated Urinary Tract Infection).

In addition, the presence of a large amount of residual urine in the bladder, added to the weight of the balloon (one gram for each c.c. of the injected sterile fluid, with usually 20 c.c.-30 c.c. of the sterile fluid 25 being injected in the bladder), and the Foley catheter weight (approximately 18 grams) leads to a substantial total weight of the indwelled catheter which causes a constant urge to the patient to urinate, and may develop spasms in the bladder and the urethra. In addition, this weight usually causes a constant irritation to the trigone and the bladder neck. This may also add to the CAUTI condition.

Another type of the urinary catheter widely used is a No-Balloon "Lotus" catheter, which has been clinically tested, and demonstrated its ability to eliminate some of the problems associated with the use of the Foley catheter.

As shown in FIGS. 2A, 2B, and 2C, the No-Balloon "Lotus" urinary catheter 40 has a catheter tube 42 extending between the proximal end 44 and the distal end 46 of the catheter. As shown in FIG. 2A, depicting the catheter 40 in its passive configuration, at the proximal end 44, the catheter 40 is provided with several, usually two-four, longitudinal slits 48 situated between portions 58 of the catheter's walls.

In proximity to the distal end 46, the catheter 40 is provided with plastic bellows portion 50. The bellows portion 50 is shown in FIG. 2A in its closed position (compressed state) when the catheter either is not in use or during introduction of the non-balloon catheter into the bladder 56 (or removal therefrom) through the urethra 55, with the tip of the proximal end 44 of the catheter 40 being introduced through the urethra 55 into the urinary bladder 56. The urine drainage port 52 at the distal end 46 is connected to, and terminates in a urine collection bag 54.

A plastic rod 60 is installed inside the catheter tube 42. The plastic rod is secured (glued or otherwise adhered), at its opposite ends, to the tip of the catheter (at the proximal end 44) and to the bellows portion 50, respectively.

Upon introduction of the No-Balloon "Lotus" catheter 40 (in its closed position shown in FIG. 2A) into the bladder 56, the catheter 40 is activated by pulling apart (stretching) the plastic bellows portion 50. Stretching of the bellows portion 50 causes displacement of the plastic rod 60 toward the distal end 46. The displacement of the plastic rod 60 results in pulling the tip 44 of the catheter 40 down so that the Maelcot (or flower) configuration 62 is formed by the folded segments (wings) 58 of the catheter tube 42 between the longitudinal slits 48 at the proximal end 44 of the catheter, as shown in FIGS. 2B-2C.

As seen in FIGS. 2B-2C, the flower configuration 62 is formed by the elastic material (wing portions 58) of the catheter tube 42 at the proximal end 44 separated by the expanded (open) slits 48. The flower configuration 62 represents a deployed configuration, which supports the indwelling of the No-Balloon "Lotus" urinary catheter 40 within the urinary bladder 56.

When the slits 48 are opened, and the elastic segments 58 between the slits 48 fold to form the flower configuration 62, a drainage opening 64 of the catheter tube 42 is exposed as the result of the fully deployed flower configuration 62. The drainage opening 64 is fluidly connected to the exhaust port 52 at the distal end 46 of the tube 42 of the catheter 40. The urine 53 is drained from the bladder 56 through the drainage opening 64 and internally of the tube 42 of the No-Balloon "Lotus" catheter 40, and exits through the urine exhaust port 52 into the urine collection bag 54.

The bellows portion 50 is shown in FIGS. 2B and 2C in the deployed (expanded or stretched) position. When the No-Balloon "Lotus" catheter 40 is to be removed from the bladder 56, the bellows portion 50 is retracted from the open position (shown in FIGS. 2B and 2C) into its closed (compressed) position (shown in FIG. 2A), thus returning the catheter 40 to the passive configuration shown in FIG. 2A.

Although the No-Balloon "Lotus" catheter 40 has been demonstrated to eliminate some of the problems associated with the Foley balloon catheter 10, there are still shortcomings which must be addressed.

For confused patients suffering from dementia, psychotic patients, or during procedures which need continuous irrigation, a catheter which can withstand inadvertent removal by a patient is required. In addition, procedures requiring an additional channel for continuous irrigation need a reliable retention of the catheter with no risk of inadvertent removal.

The No-Balloon "Lotus" catheter, although solving many of the problems of prior art devices, needs a reliable retention mechanism which would be capable of withstanding inadvertent removal. The No-Balloon "Lotus" catheter can be removed by a patient under anesthesia or under heavy sedation. This may cause various surgical complications to the patient, and may undermine the surgical procedure itself, as well as make continuous irrigation difficult.

Thus, it would be highly desirable to provide a urinary catheter which is free of the deficiencies of the Foley balloon urinary catheter, and improves operability of the No-Balloon "Lotus" urinary catheter presented supra.

It would be highly desirable to provide a urinary catheter with an improved retaining (retention) mechanism which would be safe and reliable, which can withstand attempts of inadvertent removal and, which, at the same time, causes minimal damage to the bladder and urethra when removed in a deployed configuration.

Also, it would be highly desirable to provide a urinary catheter which leaves no residual urine in the bladder after the urine drainage procedure.

In addition, it would also be highly desirable to provide a superior urine flow rate, which is important for a sufficient drainage and reduction of CAUTI occurrences.

SUMMARY OF THE INVENTION

It is therefore an object of the present invention to provide a surgical catheter for insertion and indwelling in a bodily cavity of a patient which has improved retaining capabilities to withstand an attempt of inadvertent removal.

It is another object of the present invention to provide a urinary catheter which is safe for patients and causes minimal (or no) trauma to the patient's body when inadvertently withdrawn from the bladder.

It is a further object of the present invention to provide a urinary catheter having a urine drainage port located in proximity to the bottom of the bladder (or at the bladder neck) when the catheter is indwelled within the bladder, which facilitates in a no-residual urinary drainage, thus preventing irritation to the patient and bacterial growth in the bladder.

Another object of the present invention to provide an improved urinary catheter designed based on the principles of the Lotus Catheter with the addition of a stabilizer mechanism, where in operation, when the Lotus Catheter is inserted into and is secured within the bladder, the stabilizer mechanism is used to secure the fully expanded bellows to the thigh of the patient in order to stabilize the catheter in place and prevent inadvertent removal of the catheter from the bladder.

Furthermore, it is an object of the present invention to provide a urinary catheter attaining a superior flow rate, which is achieved through a wider inside diameter of the catheter inner channel without affecting the outside diameter (or the size) of the urinary catheter.

In one aspect, the present invention is directed to a surgical catheter adapted for insertion into a bodily cavity of a patient. The subject catheter is designed with an elongated catheter body having walls extending between a proximal end and a distal end of the elongated catheter body. The walls of the elongated catheter body define an internal channel extending along a longitudinal axis of the elongated catheter body.

The catheter has first retention mechanism positioned at the proximal end of the elongated catheter body. The first retention mechanism is actuated subsequent to the proximal end of the elongated catheter body insertion in the bodily cavity of interest. The first retention mechanism is configured with a substantially cylindrically shaped retention body and a reinforcement mechanism forming reinforced walls of the retention body.

The subject catheter further includes a stabilizer mechanism which secures the elongated catheter body of the indwelled catheter to the patient body outside the bodily cavity. The stabilizer mechanism is removably engaged with the elongated catheter body at a predetermined area thereof between the proximal and distal ends thereof subsequent to actuation of the first retention mechanism.

The reinforced walls of the retention body define the retention body's internal channel which extends along the longitudinal axis of the retention body. The reinforced walls of the retention body are formed by at least two wall portions of the reinforced walls. The two wall portions have wall side edges extending longitudinally and forming at least two respective longitudinal slits extending in spaced apart relationship along the at least two wall portions, which extend between a common tip of the retention body and the proximal end of the elongated catheter body. The retention body is secured to the proximal end of the elongated catheter body with the internal channel of the retention body positioned in alignment with the internal channel of the elongated catheter body along their common longitudinal axis.

The internal channel of the retention body terminates in a drainage port positioned substantially at a bottom of the bodily cavity and beneath the first retention mechanism. The drainage port is in fluid communication with an exhaust port of the catheter which is defined by an edge of the walls of the elongated catheter body at the distal end thereof.

When positioned in the bodily cavity, the first retention mechanism is actuated to assume a deployed configuration causing elastic bending and radial outward displacement of the at least two wall portions of the reinforced walls of the retention body one from the other, resulting in opening of the longitudinal slits and exposure of the drainage port of the inner channel of the retention body to a fluid collected in the bodily cavity to withdraw the fluid therefrom through the inner channels of the retention body and the elongated catheter body, respectively, towards the exhaust port positioned at the distal end of the elongated catheter body.

The reinforcement mechanism may include at least two elongated reinforcement members, each secured (by any suitable mechanism) to a respective one of the at least two wall portions of the walls of the retention body and extending along the length thereof.

Alternatively, the reinforcement mechanism is provided by forming the walls of the retention body from a layer of an elastic material having a thickness larger than the thickness of the walls of the elongated catheter body.

The subject surgical catheter further includes a bellows unit formed at the elongated catheter body in proximity to the distal end thereof.

A plastic rod is coupled, at one end thereof, to the common tip of the retention body, and, at another end thereof, to the bellows unit.

When the bellows unit is expanded, the rod is displaced towards the distal end of the elongated catheter body causing a controlled displacement of the common tip of the retention body, thus resulting in actuation of the first retention mechanism and transformation thereof into the deployed configuration. In the deployed (active) configuration, the wall portions of the retention body are displaced radially and outwardly one from another, to assume a curved wing-like configuration abutting against the inner walls of the bodily cavity, thus anchoring the catheter therein.

The stabilizer mechanism is actuated subsequent to deployment of the first retention mechanism to engage the bellows unit to stabilize the elongated catheter body in a fixed position.

The stabilizer mechanism may have numerous configurations. For example, it may include an adhesive pad for securement to the patient's body, and a stabilizer housing attached to the adhesive pad. The stabilizing housing may be formed with a bottom wall and an upper wall displaceably secured to the bottom wall. The bottom and upper walls form a receiving channel therebetween extending longitudinally along the stabilizer housing. Once the catheter is indwelled in the body cavity with the first retention mechanism actuated, the bellows unit may be removably secured in the receiving channel between the bottom and upper walls of the stabilizer housing.

The subject surgical catheter system further comprises a urine collecting bag attached to the exhaust port of the elongated catheter body. The system drainage port and the inner channels of the retention body and elongated catheter body, respectively, form a urine passage from the bodily cavity to the exhaust port.

The subject surgical catheter is configured to operate intermittently in a passive mode of operation and in a deployed mode of operation. In the passive mode of operation, the surgical catheter is configured for removal from or for insertion into the bodily cavity. While in the passive mode of operation, the wall portions of the retention body extend substantially in parallel to the longitudinal axis thereof, thus assuming a configuration most suitable for insertion of the catheter into or removal from the body cavity.

The wall portions of the retention body may be formed integral with the walls of the elongated catheter body. Alternatively, the wall portions of the retention body are secured (glued or welded) to the walls of the elongated catheter body.

The subject surgical catheter further includes a multi-port valve mechanism positioned at the distal end of the elongated catheter body in fluid communication with the inner channel of the retention body to open the passage for urine from the bladder when a pressure in the bladder reaches a predetermined level.

In another aspect, the present invention is directed to a method for operating an improved surgical catheter through the steps of:

configuring the surgical catheter with an elongated catheter body having walls extending between proximal and distal ends thereof, defining an internal channel by the walls and extending between along a longitudinal axis of the elongated catheter body; and forming a first retention mechanism at the proximal end of the elongated catheter body. The first retention mechanism has a retention body which is configured with the walls extending between a tip and an opposite edge and defining an internal channel of the retention body.

The method further assumes the steps of:
forming the first retention mechanism with at least two wall portions of the walls of the retention body interrupted by at least two longitudinal slits extending in a spaced apart relationship along the wall portions a predetermined length thereof, and reinforcing wall portions of the retention body.
The subject method further includes:
providing the internal channel of the retention body, at one end thereof, with a drainage port positioned beneath a bottom of the first retention mechanism in fluid communication with an exhaust port positioned at the distal end of the elongated catheter body, forming a bellows unit at the elongated catheter body between the proximal the distal ends thereof, attaching a plastic rod, at one end thereof, to the tip of the retention body, and at another end thereof, to the bellows unit; and operating the catheter intermittently in a passive mode of operation and in an active mode of operation.

The subject method further continues by:
inserting the catheter, in the passive mode of operation, into a bodily cavity of interest; and subsequent to inserting said catheter in the bodily cavity, transforming the catheter in the active mode of operation by:
extending the bellows unit, thus causing displacement of the rod towards the distal end of the elongated catheter body, and displacing the tip of the retention body, thus transforming the first retention mechanism into the deployed configuration.

The subject method further includes the steps of:
securing a second retention mechanism to a patient's body, and engaging the second retention mechanism with the bellows unit to stabilize the elongated catheter body in position.

The subject method is further contemplated by executing the steps of:
configuring the second retention mechanism with an adhesive pad and a stabilizer housing unit,
attaching the adhesive pad to the patient body, and securing the stabilizer housing unit to the adhesive pad;

forming the stabilizing housing with a bottom wall and an upper wall attachable to the bottom wall, where the bottom and upper walls form a receiving channel therebetween longitudinally extending along the stabilizer housing; and subsequently to indwelling the catheter in the bodily cavity with the first retention mechanism activated, securing the bellows unit in the receiving channel between the bottom at upper walls of the stabilizer housing unit.

These and other objects of the present invention will become more apparent from reading the Detailed Description of the Preferred Embodiment(s) of the present invention in conjunction with the Patent Drawings accompanying the description.

BRIEF DESCRIPTION OF THE DRAWINGS

FIGS. 1A, 1B, and 1C are schematic representations of the prior art Foley balloon urinary catheter in a passive (FIG. 1A) and deployed (FIGS. 1B-1C) configurations, respectively;

FIGS. 2A, 2B, and 2C are schematic representations of the prior art No-Balloon "Lotus" catheter in the passive (FIG. 2A) and deployed (FIGS. 2B-2C) configurations, respectively;

FIGS. 3A, 3B, 3C, and 3D are representative of the subject urinary catheter in the passive (FIGS. 3A-3B) and deployed (FIGS. 3C-3D) configurations, respectively, with FIGS. 3B and 3D depicting reinforced wings of the retention mechanism;

DETAILED DESCRIPTION OF THE PREFERRED EMBODIMENT(S)

Figure 1A:
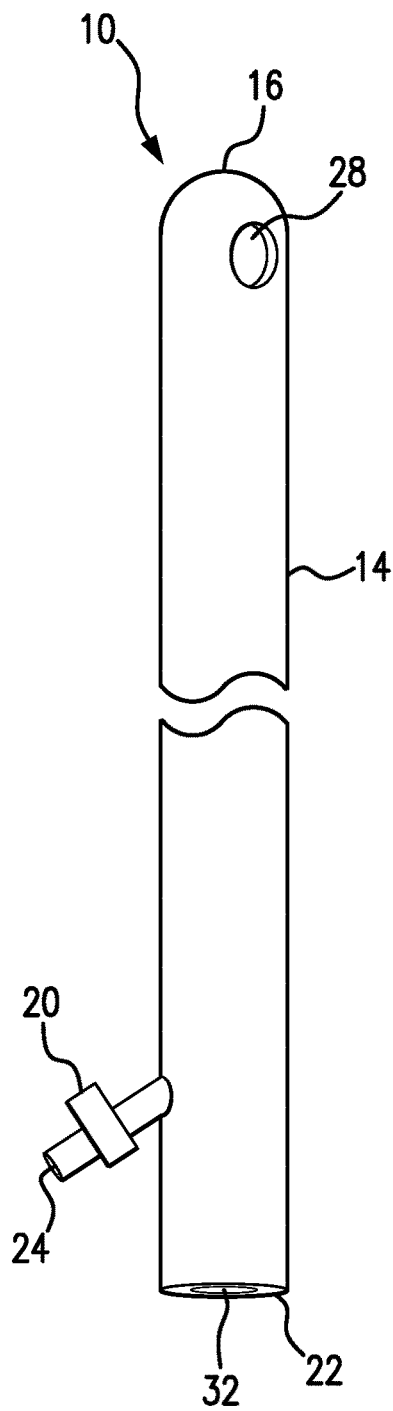

The subject catheter may be used in various surgical and therapeutic procedures, and is applicable for indwelling in various bodily cavities. However, as one of numerous exemplary applications, but not to limit the scope of the invention and the areas of its application, the subject catheter will be described herein as a urinary catheter for indwelling in the bladder of a patient, in the interest of clarity.

Referring to FIGS. 3A, 3B, 3C and 3D, the subject no-residual urine balloon catheter 100 includes an elongated tube-like catheter body 102 and a retaining (retention) mechanism 104 (also referred to herein as a first retention mechanism) positioned at a proximal end 106 of the catheter body 102. The catheter body 102 is fabricated from elastic, surgically acceptable, bio-materials, such as, for example, silicone elastomers, polyvinyl chloride (PVC), latex rubbers, etc.

A distal end 108 of the tube-like catheter body 102 is accommodated with a urine exit (or exhaust) port 110 which is positioned in fluid communication with, and terminates in a urine collection bag 112 (best shown in FIG. 3C).

As shown in FIGS. 3A and 3B, the retention mechanism 104 is configured with a retention body 113 formed with a pair (or two pairs) of longitudinal slits 114 in proximity of the proximal end 106 of the catheter body 102. In the passive configuration, the retention body 113 of the retaining mechanism 104 assumes cylindrical configuration with the longitudinal slits 114 being closed.

The tube-like catheter body 102 is formed with walls 116 defining and circumferentially enveloping an internal channel 115 of the tube-like catheter body 102.

The retention body 113 may be formed as an integral part of the tube-like catheter body 102 by cutting the elastic material of the walls 116 of the tube-like catheter body 102 a predetermined length from the proximal end 106, as shown in FIG. 3A.

Alternatively, as shown in FIGS. 3B-3D and 4A-4B, the retention body 113 may be formed as a separate cylindrically shaped elastic member (preferably, from the same surgically acceptable elastic bio-material as the material of the tube-like catheter body 102) which is permanently attached (by any suitable mechanism, such as, for example, gluing, welding, etc.) to the edge 118 of the tube-like catheter body 102 at the proximal end 106 thereof.

A bellows portion 120 is formed close to the distal end 108 of the tube-like catheter body 102. A plastic rod 122 is fastened, at one end, by any suitable mechanism to the tip 124 of the retention body 113 and, at an opposite end, to the bellows portion 120, as best shown in FIGS. 3A, 3C.

To transform into the opened (deployed) configuration, the retention mechanism 104 is actuated by extending (stretching, expanding) the bellows portion 120. This action causes the rod 122 displacement towards the distal end 108 of the catheter body 102, simultaneously bringing the tip 124 of the retention body 113 downward. The displacement of the tip 124 leads to a separating and bending of the wall portions (wings) 126 located between the slits 114, accompanied by opening of the longitudinal slits 114, thus bringing the retention mechanism 104 into the flower-like configuration 140 which constitutes a deployment configuration, shown in FIGS. 3C-3D.

Enhanced retaining qualities of the catheter are necessary when a patient suffers from dementia, is confused or recovering from anesthesia. Also, if continuous irrigation is needed, improvements to the securement mechanism of the indwelled catheter is highly beneficial for the well being of the patient.

The thickness (or stiffness) of the flower configuration 140 is directly proportional to its retainability power. The thicker (or stiffer) the flower configuration 140 is, the higher retainability by the flower configuration may be attained. Opposingly, the thinner and more elastic the flower configuration is, the weaker the retainability of the flower configuration.

As shown in FIGS. 3A-3B, better retaining capabilities can be achieved by reinforcing the flower configuration 140 with reinforcement members 128 made of a malleable material, for example, rubber or plastic with memory which in closed position are positioned parallel to the wall portions (wings) 126 of the retention body 113. The reinforcement members 128 may be welded, glued or otherwise adhered to the wings 126. The plastic rod 122 and the reinforcement members 128 may, be glued together to form a one-piece structure. The reinforced wings 126/128 will open from approximately 90 degrees up to approximately 180 degrees when the bellows 120 is stretched, as seen in FIGS. 3B-3D.

Figure 4A:
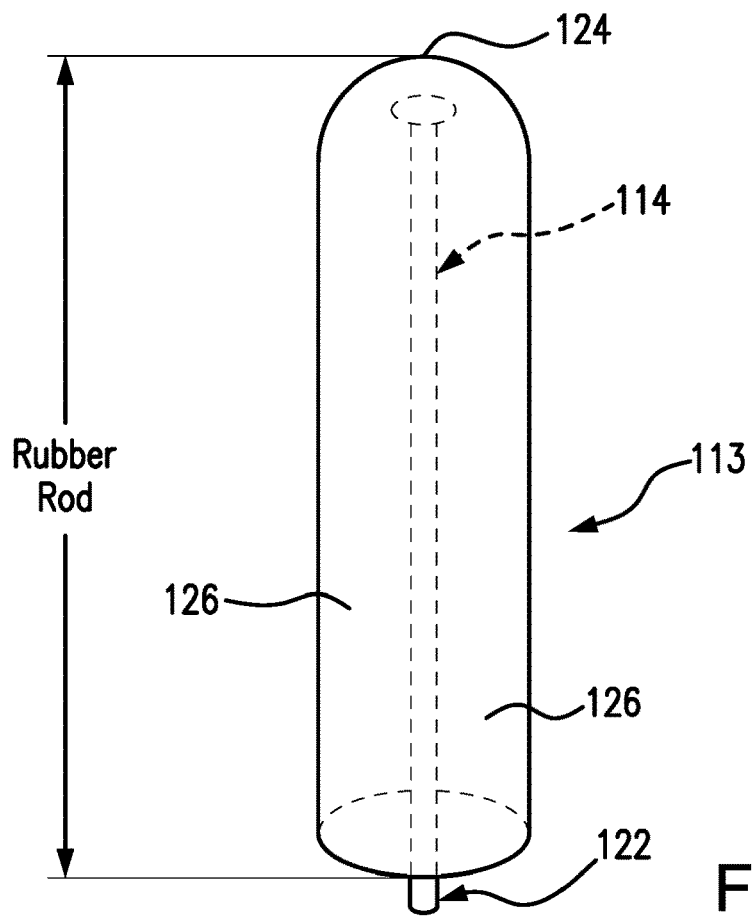
FIGS. 4A-4B are representative of the alternative embodiment of the reinforcement mechanism of the subject urinary catheter in the passive (FIG. 4A) and deployed (FIG. 4B) configurations, respectively.
Figure 4B:
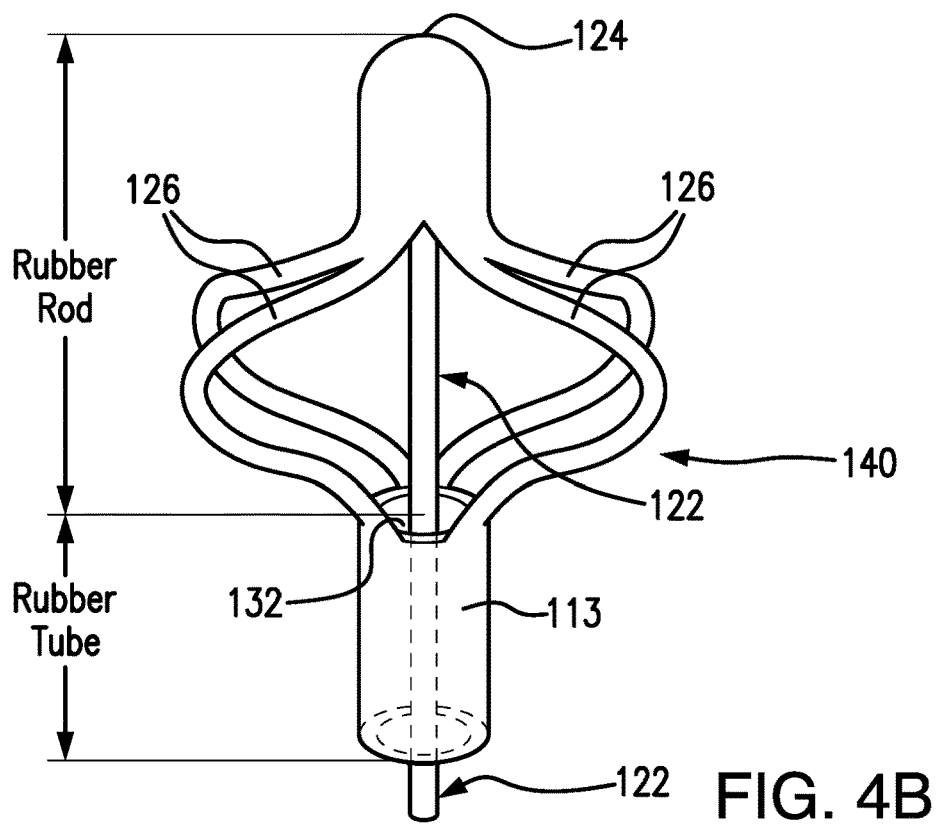

Alternatively, the retention body 113 may be injected with rubber (or similar elastomer) to change the proximal tip 124 of the Catheter 100 from a hollow tube to a solid rod, as shown in FIGS. 4A-4B. This modification makes the flower-like configuration 140 more resistant to the accidental displacement and, thus, provides an improved retainability.

It is important to note that a thicker elastic flower configuration is safer than a stiff or rigid flower configuration. In the latter example, the stiff (or rigid) flower configuration may cause damage to the bladder neck or urethra if inadvertently pulled out with the Flower Configuration in full deployment.

Therefore, it would be desirable to form only a predetermined length (for example, 5 centimeters) of the tip portion thicker, or reinforce the wings of the flower configuration with rubber or the Malleable plastic. In this manner, an improved and safer retainability may be attained compared with prior art devices, if pulled out inadvertently with the wings fully deployed.

To achieve such goal, a 5 centimeter length of the retention body 113 is either reinforced at the inner diameter (FIG. 3B, 3D), or the inner diameter of the retention body 113 is filled along the length of 5 centimeters (FIGS. 4A-4B) with rubber, for example, through injection or dipping. This process is beneficial in preserving a uniform outside diameter through the entire length of the elongated catheter body of the subject Catheter 100.

In addition to the improved retainability which may be attained due to the reinforcing of the retention mechanism 104, a second retaining mechanism 142 is provided in the subject catheter system 100. The second retaining mechanism 142 provides a stabilizing function for the indwelled catheter, and thus is also referred to herein as a stabilizer mechanism added for enhanced retainability. The stabilizer mechanism is detailed in further paragraphs related to the description of FIGS. 3C, and 6A-6E.

The subject catheter 100 is operated in two modes which include a passive (collapsed) mode of operation (shown in FIGS. 3A-3B and 4A) and an active (deployed) mode of operation (shown in FIGS. 3C-3D and 4B).

In the passive mode of operation, the retention body 113 of the retention mechanism 104 has a straight (cylindrical) configuration, with wall portions (wings) 126 disposed substantially in parallel to the longitudinal axis of the tube-like catheter body 102 with the longitudinal slits 114 closed. The passive configuration of the subject catheter 100 corresponds to the operational mode of the catheter assumed for insertion into or removal from the urinary bladder.

Upon insertion into the bladder 134, the catheter 100 is transformed into the active mode of operation for anchoring the catheter 100 in place by actuating (deploying) the retention mechanism 104, as shown in FIGS. 3C-3D, 4B and 5.

The walls wall portions (wings) of the retention body 113 cylindrically extend in the passive mode of operation and define an internal channel 130 of the retention body 113 which extends in a fluid communication and is aligned with the internal channel 115 of the tube-like catheter body 102, Both channels 115 and 130, being in alignment each with the other, form a passage for the urine 135 to move from the urine drainage port 132 (at the bottom of the retention body 113 of the retention mechanism 104) to the urine exhaust port 110 at the distal end 108 of the tube-like catheter body 102 to terminate in the urine collection bag 112 (shown in FIG. 3C).

During the procedure of inserting the catheter 100 into the bladder 134 through the urethra 136 for surgical and/or therapeutic purposes, the tip portion 124 of the retention body 113 is inserted into and is gently pushed through the urethra 136 until it enters the bladder 134. Once in the bladder 134, the catheter 100 is secured in its indwelling position by the actuated retention mechanism 104.

In order to actuate the retention mechanism 104, the bellows 120 are separated apart by a physician, and the rod 122 secured (glued) to the tip 124 as well as to the distal end 138 of the bellows 120 displaces towards the distal end 108 of the catheter 100. Subsequently, the reinforced wings 126 spread outwards, thus forming a strong flower-like configuration 140, shown in FIGS. 3C-3D, 4B, and 5.

As shown in FIG. 3C, the urine drainage port 132 is positioned in the most dependent lowest part of the urinary bladder 134. This arrangement is beneficial for a complete drainage of the urine 135 from the bladder 134, where essentially no residual urine is left in the bladder.

An improved flow rate is attained by enlarging the diameter of the internal channel of the subject catheter without affecting the outside diameter.

Improved drainage in the subject Catheter is achieved by (a) positioning of the drainage site at the most dependable part of the urinary bladder, and (b) providing a wider internal channel within the Catheter.

Figure 1B:
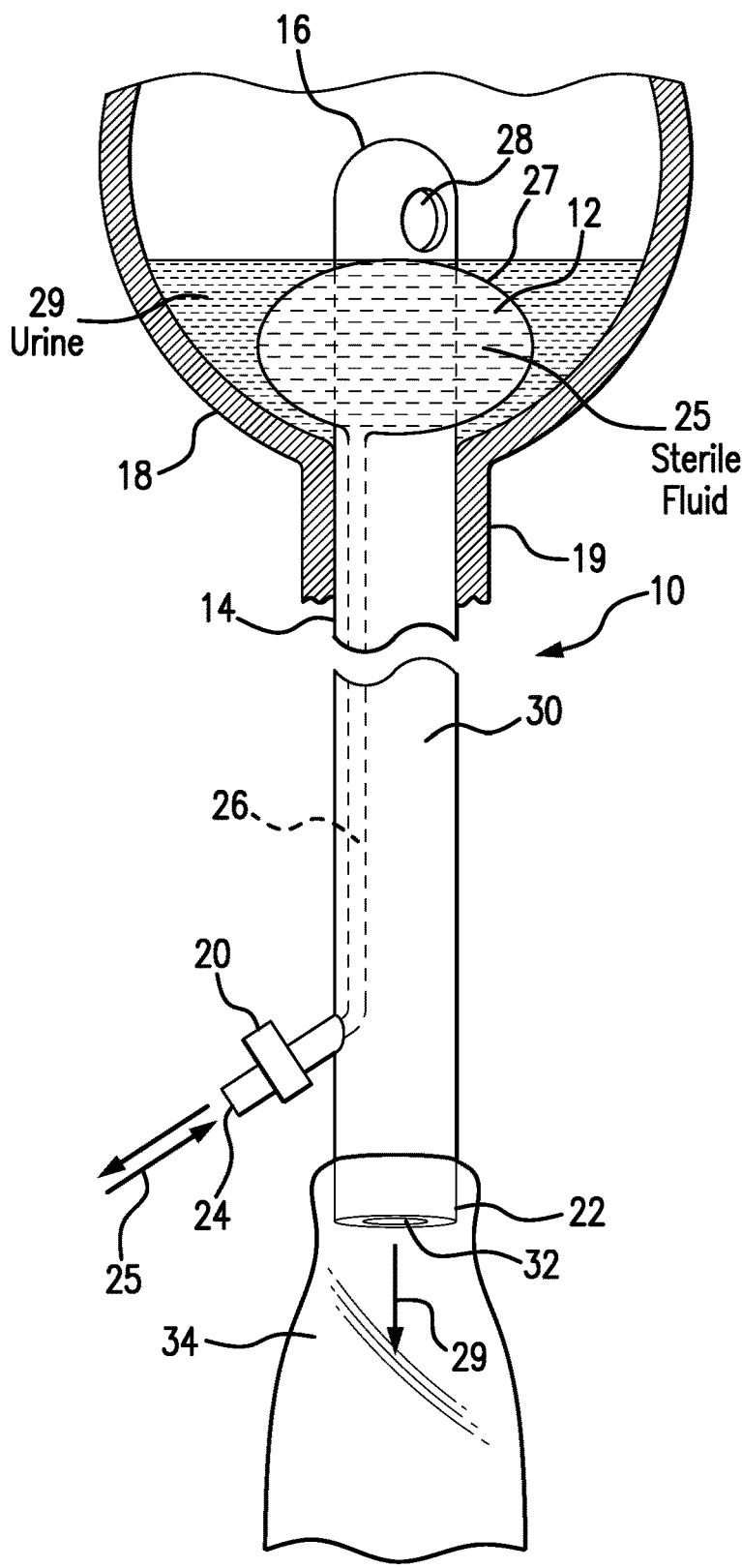
Figure 5:
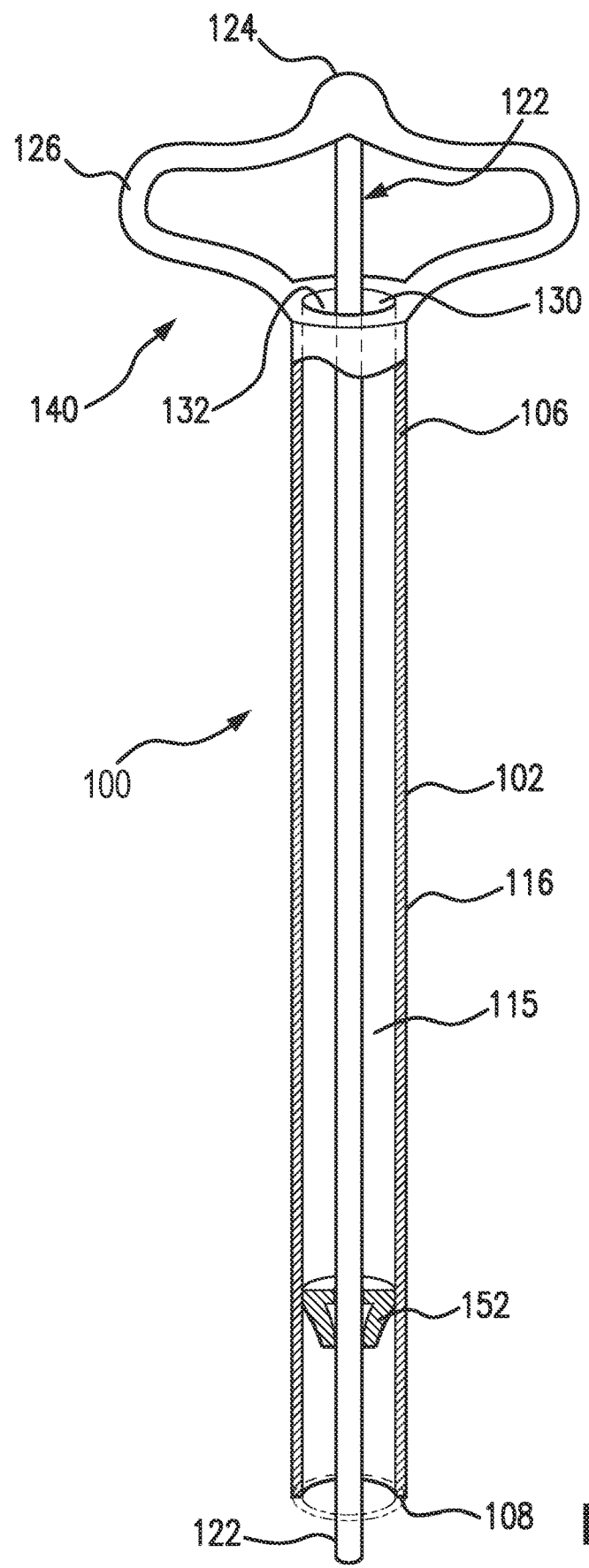
FIG. 5 shows the longitudinal section of the subject urinary catheter having a wide inner channel.

The urine drainage port 132 is wider in the subject catheter when taken with respect to prior art devices, having a diameter of the entire inner channels 130 and 115 (which is wider than the internal diameter of a conventional Foley Catheter) since no other structure obstructs the inner channels 115, 130, as shown in FIG. 5 (in comparison with FIG. 1B). Therefore, a faster drainage of the urine from the bladder 134 and a faster urine flow through the catheter 100 into the urine bag 112 can be attained, which is beneficial for lowering the incidence of CAUTI.

The positioning of the urine drainage port 132 of the subject catheter 100 at the bottom of the bladder 134 provides a complete no-residual urine drainage from the bladder 134, coupled with faster drainage of the urinary bladder, and a faster flow through the inner channel 130 of the retention body aligned with the inner channel 115 of the tube-like elongated body 102, thus eliminating conditions favorable for developing irritation and bacteria growth inside the bladder, as well as other urinary passages, that is highly beneficial for the health of the patient.

In order to provide improved retainability, in addition to the retention mechanism 104 which includes the wings 126 reinforced by the member 128, or thickened wings 126, to attain a secure retention of the catheter 100 in the bladder 134, the subject Catheter 100 is envisioned to operate with the stabilizer mechanism 142, depicted in FIGS. 3C and 6A-6E.

The stabilizer mechanism is fixed to the thigh (or other part) of the patient body by an adhesive breathable material 143, such as, for example, an adhesive pad. The stabilizer mechanism may be formed in numerous configurations providing a securement of the catheter's body 102 of the indwelled catheter 100 to the patient's body.

Figure 6A:
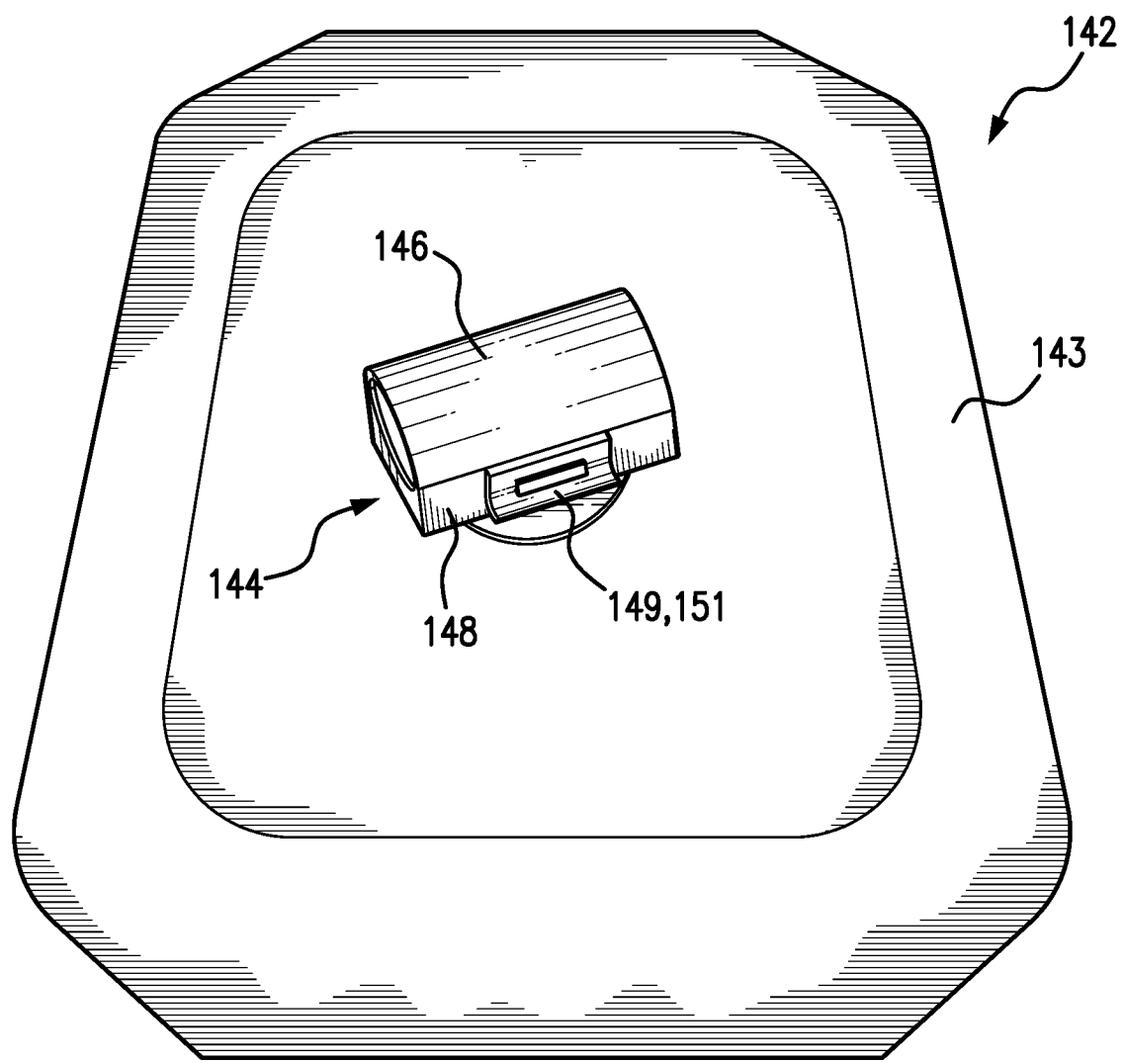
FIGS. 6A, 6B, 6C, 6D, and 6E depict the Stabilizer unit of the subject improved Lotus Catheter in the closed position (FIG. 6A) and the open position (FIGS. 6B-6C); as well as showing the open stabilizer unit with the bellows of the deployed subject urinary catheter received therein (FIG. 6D), and the stabilizer unit securing the bellows of the deployed subject urinary catheter (FIG. 6E).
Figure 6B:
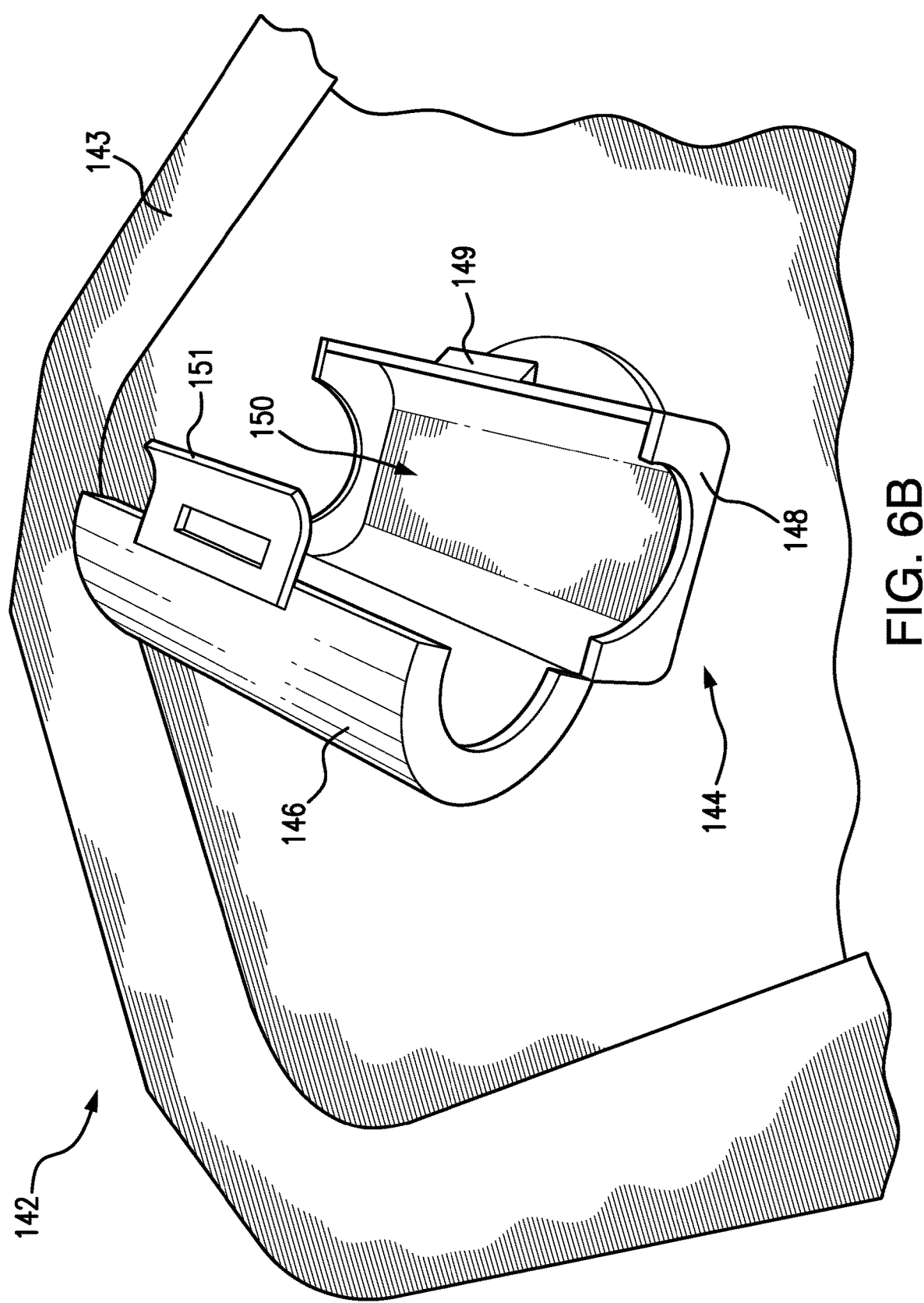
Figure 6C:
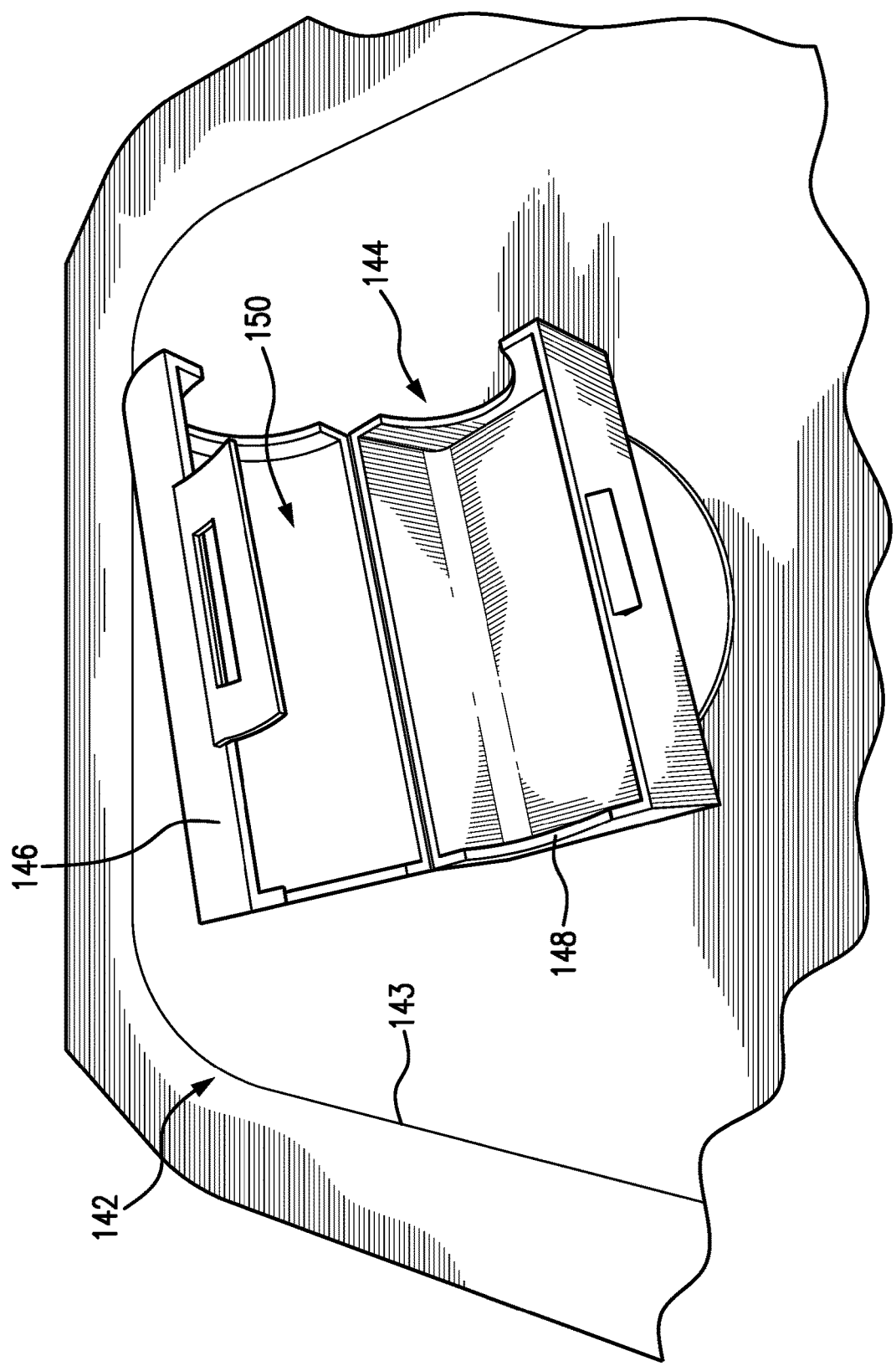
Figure 6D:
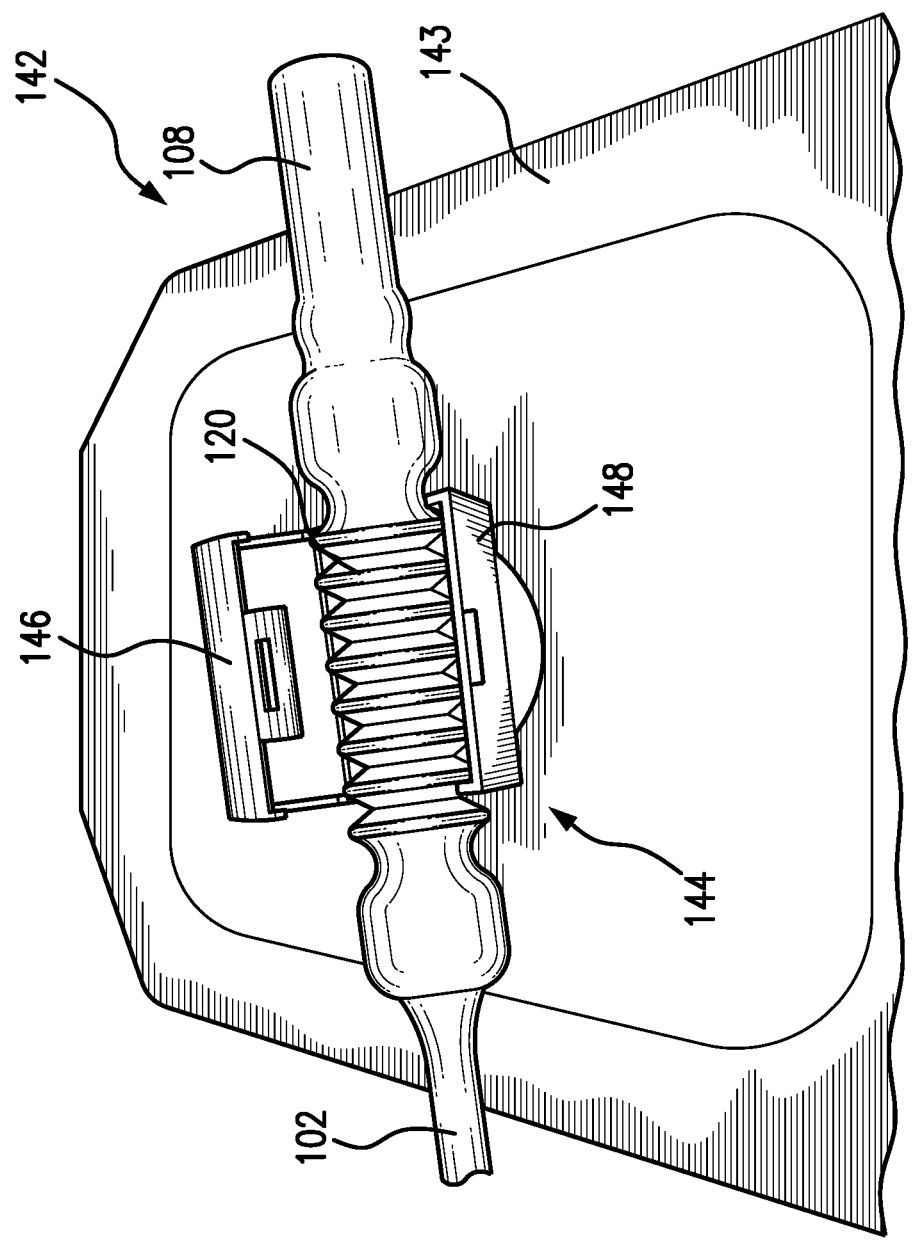
Figure 6E:
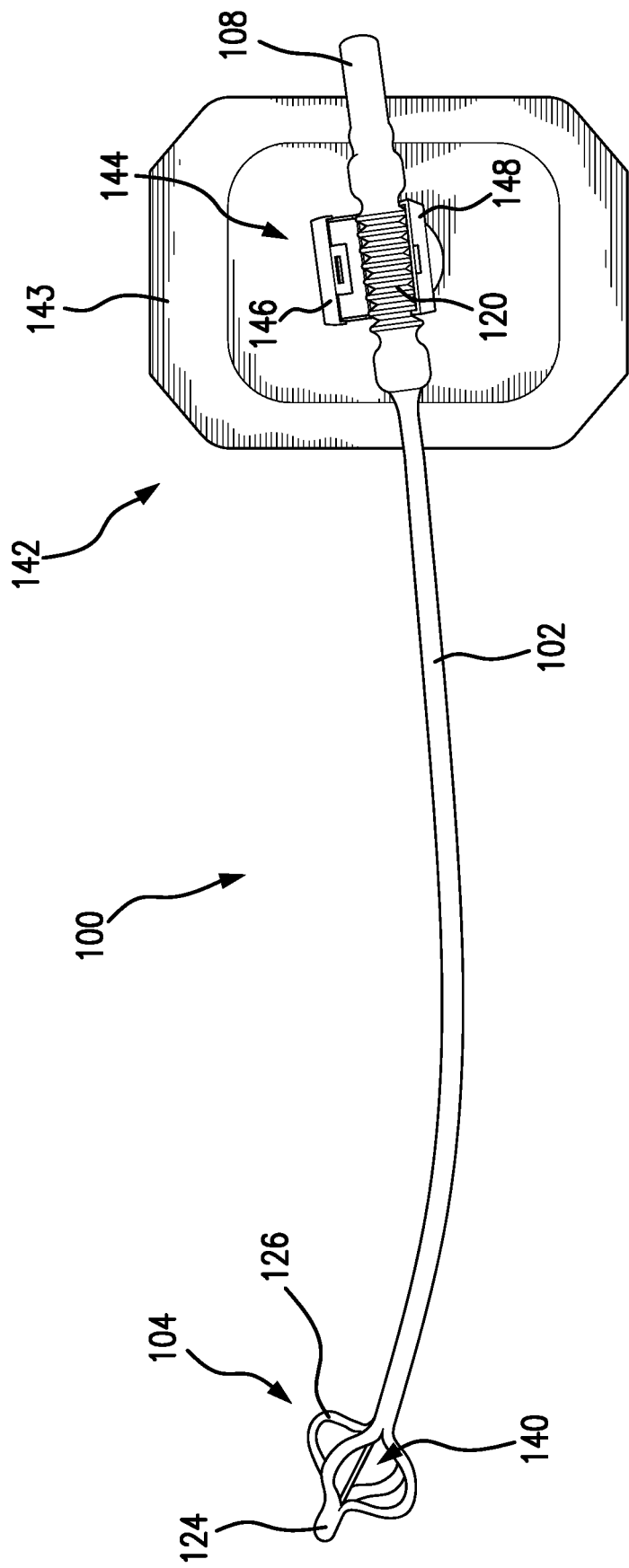

As one of numerous examples, the stabilizer mechanism 142 will be described as formed with a rotating housing unit 144 attached to the adhesive material 143 to house the bellows 50 when fully expanded, as shown in the FIGS. 3C, 6D-6E. This will prevent the patient from interfering with the Lotus Catheter.

The stabilizer 142 provides the Catheter 100 with an enhanced retainability, by preventing a direct impact of the patient's actions to the bladder neck of the patient and to secure the indwelled catheter in position.

The stabilizer housing 144 may include a bottom (or lower) wall 148 and an upper wall 146 displaceably (or removably) secured to the bottom wall 148. The walls 146, 148 may be connected, for example, by a hinge-like connection along one side of the housing 144, with a latching mechanism 149, 151 on another side of the housing.

A receiving channel 150 is formed between the walls 146, 148 to receive the bellows 120 therein to be locked between the walls 146, 148, when needed, to provide an enhanced stabilization of the indwelled catheter 100.

In order to intentionally remove the catheter 100 from the bodily cavity, as required by the surgical procedure, the stabilizer housing 144 is opened by unlocking the latching mechanism 149, 151, and hingedly separating the upper wall 146 from the lower wall 148, and the bellows 120 is removed from the receiving channel 150 of the stabilizer housing unit 144.

Subsequently, the bellows 120 is compressed, so that the rod 122 secured to the tip 124 and the distal end 138 of the bellows 120 is displaced in the direction away from the distal end 108 of the catheter body 102. This action causes return of the wings (walls) 126 in the retention mechanism 104 to their straight configuration, and closes the longitudinal slits 114, so that the catheter 100 is transformed into the passive configuration shown in FIG. 3A. In the passive configuration, the catheter 100 can be safely removed from the bladder 134 through the urethra 136.

In a catheter which has to be indwelled for months, or years, in chronic cases, it is important to maintain the physiology of the urinary bladder 134, i.e., expansion and relaxation of the bladder wall. The expansion and relaxation of the bladder wall should prevent the urinary bladder from becoming fibrotic (very small capacity bladder). In the permanently indwelled urinary catheter, it is advantageous to add a valve to the urine exiting port connected to the urine bag, which would support the release of urine when the bladder is partially filled, i.e., to attain a certain bladder pressure, thus mimicking a normal physiological process. In normal physiological condition, the bladder is slowly distended until a person empties his/her bladder. Subsequently to emptying the bladder, the bladder wall returns to its collapsed position.

The one-way pressure controlled valve 152 shown in FIG. 5 is beneficial to those patients who are deemed to have an indwelling catheter for months, years, or for life. This valve opens at a predetermined pressure of 5-8 centimeter of water, thus allowing the bladder which is partially filled with urine to empty when the bladder exceeds a predetermined pressure.

As shown in FIG. 5, the subject catheter does not use any internal tubing inside the channel 115 of the catheter body 102 (as opposed to the Foley catheter shown in FIG. 1B). The space utilized by the side port 26 in the Foley Catheter (FIG. 1B), is utilized in the subject Catheter to increase the inner diameter of the tube 102. The inside diameter of the catheter 100 is at least 20%-30% wider when compared with the Foley Catheter (FIG. 1B), which is beneficial for achieving a superior flow rate in the present Silicone Catheter 100.

A method to manufacture the Silicone Lotus Catheter (hollow tube) 100 may be through extrusion. The subject Lotus Catheter can be extruded with a large inside diameter without affecting the outside diameter. The Lotus Catheter does not need to use an inside channel tube to carry fluids to and from the balloon if compared to the Foley Catheter, and thus, the entire inner channel of the Lotus Catheter can be used for carrying fluids therethrough.

The increased inner diameter in the improved Catheter 100 also contributes to increase of the diameter of the draining port 132. Thus, a better drainage is achieved in comparison with the conventional urinary catheters.

In comparison with the conventional Foley catheter, shown in FIGS. 1A-1C, which has the drainage port positioned above the balloon, and thus does not provide a complete urine drainage from the bladder, the drainage port in the subject catheter is positioned at the very bottom of the bladder, and thus provides complete removal of the urine from the bladder, thereby eliminating the source of infection and possible irritation of the bladder.

Further, in comparison with the conventional No-Balloon "Lotus" catheter, shown in FIGS. 2A-2C, the subject surgical catheter has a reinforced or thickened flower configuration.

Also, the subject double retention mechanism (i.e., both the thickened or reinforced wing-like configuration, and the Stabilizer mechanism attached to the thigh of the patient) permits the subject catheter to attain a higher reliability than that of the conventional No-Balloon "Lotus" catheter, and thus can withstand inadvertent pulling of the catheter out.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A surgical catheter adapted for insertion into a bodily cavity of a patient, comprising:
    an elongated catheter body having walls extending between a proximal end and a distal end of said elongated catheter body, wherein said walls of said elongated catheter body define an internal channel extending along a longitudinal axis of said elongated catheter body;
    a first retention mechanism positioned at said proximal end of said elongated catheter body, said first retention mechanism being actuated subsequent to insertion of said proximal end of said elongated catheter body in a bodily cavity of interest, and
    a second retention mechanism configured to be secured to a patient's body outside the bodily cavity and engageable with said elongated catheter body subsequent to actuation of said first retention mechanism;
    said first retention mechanism being configured with a substantially cylindrically shaped retention body, a rod coupled, at one end, to said cylindrically shaped retention body, and a reinforcement mechanism operatively coupled to said retention body and configured to form reinforced walls of said retention body, wherein said reinforced walls of said retention body are formed from a singular layer of an elastic material having a first thickness larger than a second thickness of said walls of the elongated catheter body, said reinforced walls of said retention body defining an internal channel of said retention body extending along the longitudinal axis of said retention body, wherein said reinforced walls of said retention body are formed by at least two wall portions of said reinforced walls of said retention body, said two wall portions having side edges extending longitudinally and forming at least two respective longitudinal slits extending in a spaced apart relationship at said at least two wall portions,
    said at least two wall portions extending between a common tip of said retention body and said proximal end of said elongated catheter body, wherein said retention body is secured to said proximal end of said elongated catheter body, and wherein said internal channel of said retention body is positioned in alignment with said internal channel of said elongated catheter body along a common longitudinal axis, and
    wherein said internal channel of said retention body terminates in a drainage port configured to be positioned substantially at a bottom of said bodily cavity and beneath said first retention mechanism, and in fluid communication with an exhaust port defined by an edge of the walls of said elongated catheter body positioned at said distal end of said elongated catheter body;
    wherein, when positioned inside said bodily cavity, said first retention mechanism is actuated by displacing said rod towards said distal end of said elongated catheter body to assume a deployed configuration causing elastic bending and radial outward displacement of said at least two wall portions of said reinforced walls of said retention body one from another, resulting in opening of said at least two longitudinal slits and exposure of said drainage port of said internal channel of said retention body to a fluid in said bodily cavity to substantially completely withdraw said fluid therefrom through said internal channels of said retention body and of said elongated catheter body, respectively, to said exhaust port positioned at said distal end of said elongated catheter body, said at least two wall portions of said reinforced walls of said retention body attaining a sufficient stiffness to retain a secure retention of the retention body in the bodily cavity at least in part due to said first thickness of said singular layer being greater than said second thickness of said walls of said elongated catheter body.

2. The surgical catheter of claim 1, wherein said reinforcement mechanism includes at least two elongated reinforcement members, each secured to a respective one of said at least two wall portions of said walls of said retention body and extending along the length of said retention body.

3. The surgical catheter of claim 1, further including:
a bellows formed at said elongated catheter body in proximity to said distal end thereof,
wherein said rod is coupled, at one end thereof, to said common tip of said retention body, and, at another end thereof, to said bellows,
wherein, when said bellows is extended, and said rod is displaced towards said distal end of said elongated catheter body, a controlled displacement of said common tip of said retention body results in actuation of said first retention mechanism and transformation thereof into said deployed configuration; and
wherein said second retention mechanism is actuated to engage and retain said bellows in position to stabilize said elongated catheter body.

4. The surgical catheter of claim 3,
wherein said second retention mechanism includes:
an adhesive pad for securement to the patient's body, and
a stabilizer housing unit attached to said adhesive pad, and rotatively displaceable relative thereto, said stabilizer housing unit including a bottom wall and an upper wall removably secured to said bottom wall, said bottom and upper walls forming a receiving channel therebetween longitudinally extending along said stabilizer housing unit, and
wherein, once said catheter is indwelled in the bodily cavity with said first retention mechanism actuated, the bellows, in expanded configuration, is secured in said receiving channel between said bottom at upper walls of said stabilizer housing unit.

5. The surgical catheter of claim 1, wherein said at least two wall portions of said retention body are displaced radially and outwardly one from another to assume a curved wing-like configuration abutting against inner walls of said bodily cavity, thus anchoring said catheter in said bodily cavity.

6. The surgical catheter of claim 5, further comprising a urine collecting bag attached to said exhaust port, wherein said drainage port and said internal channels of said retention body and elongated catheter body, respectively, form an unobstructed urine passage from the bodily cavity to said exhaust port.

7. The surgical catheter of claim 5, configured to operate intermittently in a passive mode of operation and in a deployed mode of operation,
wherein, in said passive mode of operation, said surgical catheter is configured for removal from or for insertion into said bodily cavity, and
wherein, in said passive mode of operation, said at least two wall portions of said retention body extend substantially in parallel along said longitudinal axis of said retention body.

8. The surgical catheter of claim 7, wherein in said passive mode of operation, said surgical catheter is configured for insertion in said bodily cavity.

9. The surgical catheter of claim 7, wherein in said deployed mode of operation, said first retention mechanism is transformed into said deployment configuration, thus anchoring said catheter in the bodily cavity.

10. The surgical catheter of claim 5, wherein said at least two wall portions of said retention body are formed integrally with said walls of said elongated catheter body.

11. The surgical catheter of claim 5, wherein said at least two wall portions of said retention body are secured to said walls of said elongated catheter body.

12. The surgical catheter of claim 1, further including a multi-port valve mechanism positioned at said distal end of said elongated catheter body in fluid communication with said internal channel of said retention body.

13. A surgical catheter adapted for insertion into a bodily cavity of a patient, comprising:
an elongated catheter body having walls extending between a proximal end and a distal end of said elongated catheter body, said walls of said elongated catheter body defining an internal channel extending along a longitudinal axis of said elongated catheter body, an edge of said walls of said elongated catheter body defining an exhaust port positioned at said distal end of said elongated catheter body; and
a substantially cylindrically shaped retention body secured to said proximal end of said elongated catheter body and having reinforced walls, said reinforced walls including a plurality of wall portions formed from a singular layer of an elastic material having a first thickness larger than a second thickness of said walls of the elongated catheter body, said wall portions each extending between a common tip of said retention body and said proximal end of said elongated catheter body, said wall portions having side edges extending longitudinally and defining a plurality of respective longitudinal slits extending in a spaced apart relationship at said wall portions, said reinforced walls defining an internal channel of said retention body extending along the longitudinal axis of said retention body, said internal channel of said retention body being aligned with said internal channel of said elongated catheter body along a common longitudinal axis, said internal channel of said retention body terminating in a drainage port configured to be positioned substantially at a bottom of a bodily cavity of interest, said internal channel of said retention body being in fluid communication with said exhaust port of said elongated catheter body,
wherein said retention body is actuated subsequent to insertion of said proximal end of said elongated catheter body in the bodily cavity of interest to assume a deployed configuration formed by elastic bending and radial outward displacement of said wall portions of said reinforced walls of said retention body one from another, resulting in opening of said longitudinal slits and exposure of said drainage port of said internal channel of said retention body to a fluid in the bodily cavity to substantially completely withdraw said fluid therefrom through said internal channels of said retention body and of said elongated catheter body, respectively, to said exhaust port of said elongated catheter body, said wall portions of said reinforced walls of said retention body having a sufficient stiffness to retain a secure retention of the retention body in the bodily cavity at least in part due to said first thickness of said singular layer of said wall portions being greater than said second thickness of said walls of said elongated catheter body.

\* \* \* \* \*